United States Patent [19]

Callahan

[11] 4,309,310

[45] Jan. 5, 1982

[54] CATALYTIC COMPOSITION FOR ALLYLIC OXIDATION OF OLEFINS

[75] Inventor: James L. Callahan, Wooster, Ohio

[73] Assignee: Standard Oil Company, Cleveland, Ohio

[21] Appl. No.: 135,570

[22] Filed: Mar. 31, 1980

[51] Int. Cl.$^3$ .............................................. B01J 31/12
[52] U.S. Cl. ........................... 252/431 P; 260/429 R; 260/438.1; 260/446; 252/431 R; 562/547
[58] Field of Search ................ 252/431 P; 260/429 R, 260/431 R

[56] References Cited

U.S. PATENT DOCUMENTS

| | | | |
|---|---|---|---|
| 2,329,707 | 9/1943 | Farrington et al. | 260/429 R |
| 2,346,155 | 4/1944 | Denison et al. | 260/429 R X |
| 2,866,732 | 12/1958 | Hoff et al. | 260/429 R X |
| 2,917,528 | 12/1959 | Ramsey et al. | 260/429 R X |
| 3,219,676 | 11/1965 | Wilkinson | 260/429 R X |
| 3,595,890 | 7/1971 | Huerta et al. | 252/431 P |
| 3,907,706 | 9/1975 | Robins | 252/431 P |
| 3,910,976 | 10/1975 | Fein | 252/431 P |
| 3,931,242 | 1/1976 | Dawans et al. | 260/429 R |

OTHER PUBLICATIONS

Chemical Abstracts 76 25379n, (1972).
Chemical Abstracts 81 177827y, (1974).

Primary Examiner—Helen M. S. Sneed
Attorney, Agent, or Firm—Gary R. Plotecher; Herbert D. Knudsen; Larry W. Evans

[57] ABSTRACT

Olefins, such as propylene, are allylically oxidized to corresponding unsaturated aldehydes and carboxylic acids, such as acrolein and acrylic acid, by contacting the olefin with molecular oxygen at allylic oxidation conditions in the presence of a trifluoroalkyl sulfonate or phosphonate catalyst, such as a catalyst formed by the reaction of vanadyl oxide and trifluoromethyl sulfonate.

6 Claims, No Drawings

CATALYTIC COMPOSITION FOR ALLYLIC OXIDATION OF OLEFINS

BACKGROUND OF THE INVENTION

1. Field of the Invention

This invention relates to catalysis. In one aspect, the invention relates to the catalytic allylic oxidation of olefins while in another aspect, the invention relates to the use of trifluoroalkyl phosphonates and sulfonates as allylic oxidation catalysts.

2. Description of the Prior Art

Unsaturated aldehydes and carboxylic acids, such as acrolein and acrylic acid, and currently valuable commodities in textile manufacture. These materials are typically prepared by the oxidation of corresponding olefins, the particular compound obtained depending upon the degree of oxidation. Many catalysts are known to be useful in this oxidation but none are completely satisfactory. Of these known catalysts, those based upon phosphomolybdic and/or vanadic acids are most familiar.

SUMMARY OF THE INVENTION

According to this invention, new phosphomolybdic and/or vanadic acid catalysts demonstrate superior activity and selectively for the allylic oxidation of olefins to corresponding unsaturated aldehydes and carboxylic acids. These catalysts can be generally described as a reaction product between a molybdyl or vanadyl oxide and a perfluoroalkyl phosphonate and/or sulfonate.

DETAILED DESCRIPTION OF THE INVENTION

The catalysts of this invention are described by the empirical formula $$M_a(RF_bX)_cM'_dO_e \qquad (I)$$

where
- M is at least one of Mo and V,
- R is an alkyl radical of 1-6 carbon atoms,
- X is $PO_3^=$ or $SO_3^-$,
- M' is at least one of Sb, Cu and Pd,
- a is a number of about 0.5 to 8,
- b is a number sufficient to satisfy all but one of the valence requirements of R,
- c is a number of about 1 to 5,
- d is a number of about 0 to 10, and
- e is a number sufficient to satisfy the remaining valence requirements of the other elements present.

Preferably, M is either molybdenum or vanadium but not both, R is an alkyl radical of 1 to 3 carbon atoms and most preferably an alkyl radical of 1 carbon atom, and M' is a combination of antimony, copper and palladium. Exemplary catalysts include the reaction products of perfluoromethyl, -ethyl, -propyl, -hexyl sulfonic and phosphonic acids with the oxides of molybdenum and/or vanadium. The reaction products can also include (d is greater than zero) various amounts of copper, palladium and/or antimony which contribute to catalyst life and durability.

In formula I when M and/or M' represent more than one element, e.g. M represents both molybdenum and vanadium and M' represents copper and antimony or copper and palladium, etc., the value of a and/or d represent the combined value of the individual elements represented by M or M', respectively. In other words when M' represents as combination of copper and antimony, d is the sum of the combination and has a positive value up to about 10.

Typically, when the valence of M is 1 and the value of a is 2, then the value of c is about 1 when X is $PO_3^=$ and the value of c is about 2 when X is $SO_3^-$.

The catalysts can be used in either the 100% active form or in a diluted form, i.e. with a support. If a support is used, any inert material can be employed with alumina, silica, titania, zirconia, etc. being representative. When a support is used, typically the active catalyst is present in an amount of at least about 20, and preferably about 30, weight percent based upon the combined weight of the active catalyst and support.

The catalysts of this invention can be prepared in any one of a number of different methods, the particular method employed being a matter of convenience. Typically, the catalysts are prepared by mixing the appropriate catalyst ingredients in the proper proportion in an aqueous mixture, drying the resulting aqueous slurry with or without a reducing agent, and subsequently calcining the product. The ingredients can be added in any order during the preparation procedure but preferably the metallic ingredients are mixed prior to the addition of perfluoroalkyl sulfonic or phosphonic acid. The ingredients employed can be the oxides, halides, nitrates, acetates or other salts of the particular metal added and particularly preferred is the use of water soluble salts of the metal components. If a support is used, the materials comprising the support can be incorporated into the catalyst along with the other ingredients or the catalytic composition may be coated and/or impregnated onto or into an inert core. After the catalyst ingredients have been combined to form an aqueous slurry, the slurry is taken to dryness and the dried solid obtained is heated in the presence of air, nitrogen or nitric oxide at temperatures between about 200° and 500° C. This calcination can take place outside the process reactor or an in situ activation can be utilized. Other methods of preparation are broadly taught in the art.

The compositions of formula I are highly effective catalysts for the allylic oxidation of olefins to the corresponding aldehyde or carboxylic acid. These catalytic compositions are used in the same manner as known catalytic compositions. The reaction is a known reaction involving generally the contact of an allylic olefin with molecular oxygen at an elevated temperature. In one particular embodiment of this invention, the novel catalytic compositions of formula I are used within the parameter of the known art process.

Any hydrocarbon or inertly-substituted olefinic hydrocarbon having an allylic carbon can be used in the practice of this invention. "Inertly-substituted" and like terms here mean that the allylic olefin can contain one or more substituents, such as alkyl, aryl, etc. which are essentially nonreactive with the reagents, catalysts and products of the process at process conditions. Exemplary of suitable allylic olefins are propylene, 1-and 2-butene, isobutene, any of the isomeric pentenes, such as 2-pentene, etc. Propylene and isobutylene are preferred allylic olefins.

Illustrative of the known allylic oxidation process is a contacting of gaseous allylic olefin, e.g. propylene, with molecular oxygen in the presence of steam at a temperature between about 200° and about 500° C., preferably between about 300° and 400° C. The ratio of reactants can vary widely with mole ratios of molecular oxygen to allylic olefin of about 1 to about 10 being typical. If desired, steam can also be used in the reaction and, if used, can vary widely from a small amount to 20 or more moles of steam per mole of allylic olefin. If steam is employed, it is preferably employed in an amount of about 1 to about 10 moles of steam per mole of allylic olefin. Molecular oxygen is most conveniently added as air.

The oxidation reaction may be conducted in a fixed-bed, fluid-bed or transfer line reactor using atmospheric, superatmospheric or subatmospheric pressure. The contact time of reactants over the catalyst can vary from a fraction of a second to 20 or more seconds, the exact time dependent upon other reaction conditions, such as catalyst composition, feed composition, temperature, pressure, reactor-type, etc.

The following examples are illustrative of certain specific embodiments of this invention. Unless otherwise indicated, all parts and percentages are by weight.

SPECIFIC EMBODIMENTS

Procedure

A flow microreactor was used in these experiments and consisted of a 5/16 in. I.D.=6⅜in. long stainless steel (ss) tubes immersed in molten salt. Feed was introduced into the bottom of the reactor through a 3/16 in. O.D. ss preheat leg. The reactor itself and preheat leg formed a U-shaped configuration. Process water was introduced through a silicone septum at the top of the preheat leg. Model 355 Sage syringe pump was used to regulate process water flow rate. The feed gases, air and propylene, were regulated at 40 and 12 p.s.i.g. respectively and were metered through Brooks R-2-15-AAA Rotameter tubes. The catalyst charge was 5 cc of 10–20 mesh particles in all experiments. The reactor effluent was scrubbed in 5 cc distilled water at ice temperature for condensible product recovery. Fixed-gas was analyzed by means of chromatographic gas partitioner (Perkin-Elmer Model 164). The aqueous solution of condensible product was analyzed for carbonyl with a Perkin-Elmer Model 3920 gas chromatograph. Total acid was determined by titration of the aqueous product with 0.1 N sodium hydroxide. Catalyst were tested at several reaction temperatures in the range of 300°–400° C. with a feed mixture of five parts air to one part propylene. Process water feed rate was standardly set at 0.06 cc/min (equivalent to 4.08 water/propylene). Total gas flow rate was 111 STP cc/min giving an apparent contact time range of about 0.6 to 1 seconds.

The catalysts here used were prepared by dissolving the halide salt of the particular metal forming the catalyst in distilled water followed by addition of the appropriate acid (either perfluoromethyl sulfonic acid or perfluoromethyl phosphonic acid). The resulting solution was heated with stirring until clear at which time Nalco 1034 silica sol was added as a support. A mixture was then evaporated to a stiff gel and the gel was oven-dried at 200° C. for approximately 2 hours. The dried gel was then calcined in air at 400° C. for an additional 2 hours. Calcined cake was subsequently crushed and screened to secure a 10–20 mesh size fraction.

The results of various experiments are reported in the Table.

TABLE

ALLYLIC OXIDATION OF PROPYLENE

| | Catalyst[1] | TEMP (°C.) | $C_3^=$ Conv.[2] | PRODUCT YIELD | | PPC[3] |
|---|---|---|---|---|---|---|
| | | | | Acrolein | Acrylic Acid | |
| Example | | | | | | |
| 1.1 | $VO(CF_3SO_3)_2$ | 325 | 4.21 | 21.9 | 59.4 | 3.42 |
| 1.2 | " | 350 | 13.39 | 13.7 | 44.6 | 7.81 |
| 1.3 | " | 375 | 21.16 | 10.9 | 45.7 | 11.98 |
| 1.4 | " | 400 | 25.38 | 13.9 | 41.3 | 14.01 |
| 2.1 | $VO(CF_3PO_3)$ | 350 | 6.95 | 9.9 | 78.8 | 6.16 |
| 2.2 | " | 375 | 12.93 | 7.7 | 64.3 | 9.31 |
| 2.3 | " | 400 | 24.46 | 7.5 | 48.1 | 13.60 |
| 3.1 | $Cu_{0.5}Pd_{0.2}MoSb_{0.15}(CF_3PO_3)O_{9.23}$ | 300 | 4.15 | 33.3 | 58.3 | 3.80 |
| 3.2 | $Cu^{0.5}Pd_{0.2}MoSb_{0.15}(CF_3PO_3)_{9.23}$ | 325 | 8.11 | 35.9 | 35.8 | 5.81 |
| 3.3 | $Cu_{0.5}Pd_{0.2}MoSb_{0.15}(CF_3PO_3)O_{9.23}$ | 350 | 22.57 | 28.5 | 28.6 | 12.89 |
| 4.1 | $(MoO_2)_2(CF_3PO_3)Mo_4O_{12}$ | 325 | 6.24 | 49.0 | 38.8 | 5.49 |
| 4.2 | " | 350 | 10.78 | 31.3 | 51.6 | 8.94 |
| 4.3 | " | 375 | 15.70 | 22.9 | 57.5 | 12.62 |
| 4.4 | " | 400 | 18.10 | 16.9 | 61.0 | 14.01 |
| Control | | | | | | |
| A.1 | $MoOSO_4$ | 325 | 3.77 | 40.6 | 32.1 | 2.74 |
| A.2 | " | 350 | 2.94 | 36.4 | 43.9 | 2.36 |
| A.3 | " | 375 | 1.57 | 38.9 | 46.5 | 1.34 |
| A.4 | " | 400 | 2.49 | 43.0 | 32.5 | 1.88 |

[1]All catalysts 20% active except for $VO(CF_3PO_3)$ which is 10% active.
[2]Propylene conversion.
[3]Per pass conversion = (acrolein + acrylic acid) ($C_3^=$ conv.)

The tabulated data demonstrate the efficiency of the catalysts of this invention. These catalysts show better activity and generally better selectivity for useful products than the control catalysts, particularly evidenced by the PPC.

Although the preceding examples describe this invention in considerable detail, this detail is for the purpose of illustration only and is not to be contrued as a limitation upon the invention as described in the specification or following claims.

The claimed invention is:

1. A catalytic composition of the empirical formula $$M_a(RF_bX)_cM'_dO_e \qquad (I)$$

where

M is at least one of Mo and V,

R is an alkyl radical of 1-6 carbon atoms,

X is $PO_3^=$ or $SO_3^-$,

M' is at least one of Sb, Cu and Pd, a is a number of about 0.5 to 8, b is a number sufficient to satisfy all but one of the valence requirements of R, c is a number of about 1 to 5, d is a number of about 0 to 10, and e is a number sufficient to satisfy the remaining valence requirements of the other elements present.

2. The composition of claim 1 where M is either Mo or V but not both.

3. The composition of claim 2 where R is an alkyl radical of 1 carbon atom.

4. The composition of claim 3 where d is greater than zero.

5. The composition of claim 4 where M' is a combination of Sb, Cu and Pd.

6. The composition of claim 3 selected from the group consisting of $VO(CF_3SO_3)_2$, $VO(CF_3PO_3)$, $Cu_{0.5}Pd_{0.2}MoSb_{0.15}(CF_3PO_3)O_{9.23}$ and $(MoO_2)_2(CF_3PO_3)Mo_4O_{12}$.

* * * * *